(12) United States Patent
Njemanze

(10) Patent No.: US 6,773,400 B2
(45) Date of Patent: Aug. 10, 2004

(54) NONINVASIVE TRANSCRANIAL DOPPLER ULTRASOUND FACE AND OBJECT RECOGNITION TESTING SYSTEM

(76) Inventor: Philip Chidi Njemanze, No. 1 Uratta/MCC Road, P.O. Box 302, Owerri, Imo (NG)

( * ) Notice: Subject to any disclaimer, the term of this patent is extended or adjusted under 35 U.S.C. 154(b) by 0 days.

(21) Appl. No.: 10/109,867

(22) Filed: Apr. 1, 2002

(65) Prior Publication Data

US 2003/0187359 A1 Oct. 2, 2003

(51) Int. Cl.$^7$ ................................ A61B 8/06
(52) U.S. Cl. ...................................... 600/454
(58) Field of Search ................ 600/300–595; 73/625, 626; 367/7, 11, 130, 138, 151, 191; 128/916, 731, 732, 920; 374/45; 607/17–24; 382/100, 118, 181, 190, 195, 217, 227, 243; 345/419, 427; 310/333, 334

(56) References Cited

U.S. PATENT DOCUMENTS

| | | | | |
|---|---|---|---|---|
| 5,295,491 A | * | 3/1994 | Gevins | 600/544 |
| 5,724,987 A | * | 3/1998 | Gevins et al. | 600/544 |
| 5,771,261 A | * | 6/1998 | Anbar | 374/45 |
| 6,126,595 A | * | 10/2000 | Amano et al. | 600/300 |
| 6,258,032 B1 | * | 7/2001 | Hammesfahr | 600/454 |
| 6,309,361 B1 | * | 10/2001 | Thornton | 600/544 |

* cited by examiner

*Primary Examiner*—Ali Imam

(57) ABSTRACT

A non-invasive method and system to determine face and object processing in a human subject, said method with high temporal resolution, user-friendly and portable, including steps of obtaining a subjects baseline cerebral blood flow velocity in cerebral arteries using a transcranial Doppler ultrasound instrument with sample volumes focused on cerebral vessels on both sides using two probes place on the temples and calculating laterality index for both arteries. Simultaneously, testing the subject with face and object processing tasks presented on the screen of a digital computer and using a computer input peripheral device while simultaneously monitoring the mean blood flow velocity during each stage of the task in real-time. Processing the acquired data using a microprocessor operatively connected to a computer work station for image retrieval.

20 Claims, 6 Drawing Sheets

NONINVASIVE TRANSCRANIAL DOPPLER ULTRASOUND FACE AND OBJECT RECOGNITION TESTING SYSTEM

CROSS-REFERENCE TO RELATED APPLICATION

U.S. PATENT DOCUMENTS

| U.S. Pat. No. 5,295,491 | March 1994 | Givens, Alan S. | 600/544 |
| --- | --- | --- | --- |
| U.S. Pat. No. 5,724,987 | March 1998 | Givens et al. | 600/544 |
| U.S. Pat. No. 6,309,361 | October 2001 | Thorton, Kirtley E. | 600/544 |
| U.S. Pat. No. 6,390,979 | May 2002 | Njemanze, Philip C. | 600/438 |

BACKGROUND OF THE INVENTION

This invention is related to computerized systems and methods for determining facial and object recognition using a portable non-invasive transcranial Doppler ultrasound equipment operatively connected to a microcomputer, and the system linked to a computer workstation.

In recent years development of cognitive neuroscience has sort ways to monitor facial and object recognition with the aim to identifying underlying neuropsychological mechanisms. The mechanisms involved in face and object cognition are complex and combine multi-modal memories that permit the experience of familiarity with a given face or object. It has been suggested that, face processing comprise at least three phases: the first, initial formation of a percept originating from the given face, the second phase involves matching the percept to pre-existing stored information, and the third phase involves a contextual non-verbal and/or verbal evocation as described by Kim et al, in an article titled "*Direct comparison of the neural substrates of recognition memory for words and faces*" and published in *Brain*, dated 1999, volume 122, pages 1069 through 1083.

However, monitoring facial and object recognition has not been an easy task. Currently, there is no comprehensive and universal approach for face and object recognition monitoring that could be implemented in forensic analysis or faces and objects associated with a crime scene. In other cases face and object processing could be applied in the advertisement industry to select the face on the cover of magazines or for product promotion. Similarly, the facial expression of a famous politician on a campaign poster could go a long way to create a desirable impression on voters. Other areas of application include use in plastic surgery when it becomes essential to change particular features of the face to reach a desirable target, for example an actress could wish to change some facial features to improve her sexual appeal among male fans using the brain effects evoked by the face of another famous actress. Object perception is crucial for marketing for example in the design of a new brand of car certain external features could be enhanced by using the known brain effects of these selected features from an old successful brand. To address these problems more effectively, it is important to understand the basic brain mechanisms that underlie face and object recognition. The neuroanatomical correlates of face processing have been fairly well studied. During the perception of faces, major activation occurs in extrastriate areas bilaterally, particularly in the fusiform gyri as described by Haxby et al, in an article titled "*Dissociation of object and spatial visual processing pathways in human extrastriate cortex*" published in the *Proceedings of the National Academy of Sciences of the United States of America*, dated 1991, volume 88, pages 1621 through 1625, and in the inferior temporal gyri as described by Puce et al, in an article titled "*Face-sensitive regions in human extrastriate cortex studied by functional MRI*" published in *Journal of Neurophysiology*, dated 1995, volume 74, pages 11921 through 1195. The fusiform gyrus is activated by all face-processing tasks, suggesting that this area is involved in the first phase of perceptual operations not involving encoding and retrieval of the second phase as described by Haxby et al, in an article titled "*Face encoding and recognition in the human brain*" published in the *Proceedings of the National Academy of Sciences of the United States of America*, dated 1996, volume 93, pages 922 through 927. Activation of the fusiform gyrus is non-specific and has been implicated in visual discrimination of color or shape as described by Corbetta et al, in an article titled "*Selective and divided attention during visual discriminations of shape, color, and speed: functional anatomy by positron emission tomography*" published in *Journal of Neuroscience*, dated 1991, volume 11, pages 2383 through 2402, and even by visually presented words as described by Nobre et al, in an article titled "*Word recognition in the human inferior temporal lobe*" published in *Nature*, dated 1994, volume 372, pages 260 through 263, but not by visual stimuli like checkerboards or dot patterns as described by Fox et al, in an article titled "*Mapping human visual cortex with positron emission tomography*" published in *Nature* dated 1986, volume 323, pages 806 through 809. Neuroimaging studies on the other hand, suggest that occipitotemporal regions were more active during face perception than during object perception as described by Sergent et al, in an article titled "*Functional neuroanatomy of face and object processing*" published in *Brain*, dated 1992, volume 115, pages 15 through 36, during face matching than during location matching as documented by Haxby et al (1991) and during face perception than while viewing scrambled faces as described by Puce et al (1995) or textures also described by Puce et al (1995). Thus, it has been suggested that different regions of the extrastriate cortex process different visual stimulus attributes. However, there is overwhelming evidence that neural substrates specialized for face perception, and not merely for object perception, exist in the extrastriate cortex.

Neuroimaging techniques have been applied in the study of affective aspects of face processing. In one such study increased regional cerebral blood flow (rCBF) was seen in the left anterior frontal cortex when faces were judged as unattractive, while increased rCBF was increased in the left fronto-temporal cortex when faces were assessed as attractive as described by Nakamura et al, in an article titled "*Neuroanatomical correlates of the assessment of facial attractiveness*" published in *Neuroreport*, dated 1998, volume 9, pages 753 through 757. More specifically, perceived attractiveness of an unfamiliar face increases brain activity in the ventral striatum of the viewer when meeting the persons eye, and decreases activity when eye gaze is directed away as described by Kampe et al, in an article titled "*Reward value of attractiveness and gaze*" published in *Nature*, dated 2001, volume 413, page 589. Depending on the direction of the gaze, attractiveness could thus activate dopaminergic regions that are strongly linked to reward prediction, indicating that central reward systems may be engaged during the initiation of social interactions as discussed by Kampe et al (2001). Others have documented that passive viewing of beautiful female faces by males activates reward circuitry, in particular the nucleus accumbens as described by Aharon et al, in an article titled "*Beautiful faces* have variable reward value: fMRI and behavioral evidence" published in *Neuron*, dated 2001, volume 32, pages 537 through 551. Other investigators have established in studies using PET, the role of hippocampal formation during memory of faces as described by Kapur et al, in an article titled "*Activation of human hippocampal formation during memory for faces.* A PET study" published in *Cortex*, dated 1995, volume 31, pages 99 through 108.

It has been documented using neuroimaging methods that increasing the intensity of sad facial expression was associated with enhanced activity in the left amygdala and right temporal pole as described by Blair et al, in an article titled "*Dissociable neural responses to facial expressions of sadness and anger*" Brain, dated 1999, volume 122, pages 883–893. Others have documented enhanced activity in the left amygdala, left pulvinar, left anterior insula and bilateral anterior cingulate gyri was observed during the processing of fearful faces as demonstrated by Morris et al, in an article titled "*A neuromodulatogy role for the human amygdafa in processing emotional facial expressions*" published in *Brain*, dated 1998, volume 121, pages 47–57. Conversely, a greater right hemisphere activation was seen with happy face. Other authors using other neuroimaging modalities have concluded that the right neostrum and left ainygdala were activated when subjects made explicit judgments of disgust, bilateral orbitofrontal cortex when they made judgment of happiness, and right frontal and insula cortex when the made judgments about any emotion as described by Gomo-Tempini et al, in an article titled "*Explicit and incidental facial expression processing: an fMRI study*" published in *Neuroimage*, dated 2001, volume 14, pages 465–473.

Transcranial Doppler (TCD) sonography is an ultrasound technique that uses Doppler principles to measure cerebral blood flow velocity in major brain arteries of the circle of Willis. The basic principles and common clinical applications are detailed in a book edited by Aaslid R, entitled *Transcranial Doppler Sonography* and published by Springer, of Wien, N.Y., dated 1989, on pages 39 through 50. There is increasing body of evidence that cerebral lateralization and its relations to brain function could be studied using transcranial Doppler ultrasound as shown in a series of studies by Njemanze PC, in an article titled "*Cerebral lateralization in linguistic and non-linguistic perception: analysis of cognitive styles in the auditory modality*" published in *Brain and Language*, dated 1991, volume 41, pages 367 through 380; Njemanze et al, in an article titled "*Cerebral lateralization and color perception: a transcranial Doppler study*" published in *Cortex*, dated 1992, volume 28, pages 69 through 75; Njemanze PC, in an article titled "Cerebral lateralization in random letter task in the visual modality: a transcranial Doppler study" published in *Brain and Language*, dated 1996, volume 63, pages 315 through 325; Evers et al, in an article titled "*The cerebral haemodynamics of music perception. A transcranial Doppler sonography study*" published in *Brain*, dated 1999 volume 122, pages 75 through 85; Vingerhoets & Stroobant, in an article titled "*Lateratization of cerebral blood flow velocity changes during cognitive tasks. A simultaneous bilateral transcranial Doppler study*" published in *Stroke*, dated 1999, volume 30, pages 2152 through 2158. Studies with TCD have been cross validated by functional MRI as described by Schmidt et al, in an article titled "*Determination of cognitive hemispheric lateralization by functional transcranial Doppler cross validated by functional MRI*" *Stroke*, dated 1999, volume 30, pages 939 through 945, and reproducibility assessed as described by Knecht et al, "*Reproducibility of functional transcranial Doppler sonography for determining hemispheric language lateralization*" published in *Stroke*, dated 1998, volume 29, pages 1155 through 1159. Studies with TCD suggest that facial recognition task elicited interhemispheric blood flow velocity increase greater in the right middle cerebral artery than in the left as described by Harders et al, in an article "*Brain activity and brain blood flow velocity changes: a transcranial Doppler Study*" published in *International Journal of Neuroscience*, dated 1995, volume 47, pages 91 through 102. However, matching faces presented with computer-aided display with imaginary faces for forensic analysis has not been implemented until now.

Currently, the use of imaging techniques such as positron emission tomography (PET) and fMRI could not be applied for a single subject real-time face and object recognition monitoring under normal everyday conditions. Efectrophysiological devices particularly the electroencephalography (EEG) has been used along with other physiological variables such as eye movement, scalp and facial muscle activity, heart activity, respiration and skin conductance to determine the state of mental performance in general. The patents U.S. Pat. No. 5,295,491 to Givens and U.S. Pat. No. 5,724,987 to Gevins et al, described a testing method and system for testing the mental performance capability of a human subject, which includes a digital computer workstation for presenting a test lo the subject, such as visuomotor memory task. Recently, U.S. Pat. No. 6,390,979 to Njemanze described a noninvasive transcranial Doppler ultrasound computerized mental performance testing system. The device assesses multi-modality related working memory and communicated the outcome to an operatively connected computer. U.S. Pat. No. 6,309,361 B1 to Thomton teaches method for improving memory by identifying and using QEEG parameters correlated to specific cognitive functioning wherein the cognitive abilities addressed include memory for auditory and visual (face, Korean characters, reading material).

BRIEF SUMMARY OF THE INVENTION

There is currently no objective method based on brain physiology to aid forensic analysis of faces and objects associated with crime scenes or face or object perception for advertising purposes. Crime scene analysis is usually based on face recognition of a suspect by a witness requested to match the given face in a 'line-up' or from a police database of faces of suspects. Electrophysiological and neuroimaging techniques have not been implemented for such analysis until now. There are no established governing principles for face and object recognition. Electrophysiological techniques in spite of good temporal resolution fail to define a unified set of rules governing mental performance. Neuroimaging techniques (PET and fMRI) are cumbersome and have poor temporal resolution so are not applicable for monitoring face and object perception in real-time forensic analysis. Moreover, there usefulness can be limited to identifying brain structures implicated in the process rather than providing a consistent pattern of changes to varying stimuli in one subject. In some criminal cases, the witness of a crime scene is healthy and can recollect the face seen at the crime scene, so all that is required is for the witness to match the experience of now imaginary face to that presented by computer-aided display. In other cases the witness maybe severely injured and unable to voice responses due to injury, assessment becomes difficult until after recovery. This might take too long and delay the delivery of justice. The device must be able to assess objective responses regardless of the spoken response of the witness. Moreover, some witnesses may decide not to give truthful evidence for fear of reprisals from the criminals, more especially with growing international terrorism. It is therefore essential to have reliable objective measures that will characterize responses regardless of vocalized response by the witness. In some other cases where evidence is sketchy, the police might need to produce a composite illustration of the face seen at a crime scene. A composite illustration of the face refers to making up the facial features from the separate parts that make up the face according to sketch descriptions obtained from one or several sources. Several composite drawings might need to be made to aid the witness recognize the face and subsequently to ask the public assistance in an effort to apprehend the criminal. The device must be able to assess the different levels of similarity of the composite illustration of the face to that seen by the witness. The target face is therefore known and held in memory of the witness, the composite illustration of the face could be step wisely put together using clues, and the similarity evoked at each stage in the brain response assessed until there is a match. Similarly, the search for a model could well be narrowed by forming a composite image of the desired facial features from what is known from famous faces of models and using the composite to evoke a desired brain response. The search for the model with a face that has such features could then proceed with the guidelines developed using positive brain responses. A combined effect of different makeup looks of a face could be used to improve the image of an actor or actress using the brain response pattern obtained in a selected audience. The device must be capable of assessing affective aspects of a given face.

Therefore, what is required is a non-invasive technique that is easy to use for everyday applications, and would not involve extensive wiring of the subject. Such a technique must allow acquisition of data from an imaginary face or object and matched with composite illustration of faces or objects (e.g. a gun, car, toys etc.) presented by computer-aided display or in some cases by physical display of persons or objects. The device could assess face and object memory with the aim to match the presented face or object to that held memory. In other words the device could assess face and object working memory. The device could assess the response pattern evoked by a given face or object in relation to a 'gold standard' such as the face of a famous actress or successful brand of a car or children's toys. Other utilities include assessment on how the use of color, form or shape of an object improves the brain response to the object in comparison to a gold standard. Similarly the device could be used for assessment of the enhancing effect of clothing, posture, hairstyle etc. on the response evoked by a given face.

It is an objective of the present invention to provide a method and system that uses real-time measurements of cerebral blood flow velocity in major arteries of the brain for example middle cerebral arteries to measure face recognition.

It is a further objective of the present invention to provide a method and system that uses real-time measurements of cerebral blood flow velocity in major arteries of the brain for example middle cerebral arteries to measure the response to an imaginary face.

It is a further objective of the present invention to provide a method and system that uses real-time measurements of cerebral blood flow velocity in major cerebral arteries of the brain for example the middle cerebral arteries to determine the match between a real face displayed on a computer screen with the imaginary face seen by the witness of a crime scene.

It is a further objective of the present invention to provide a method and system that uses real-time measurements of cerebral blood flow velocity in major cerebral arteries of the brain for example the middle cerebral arteries to determine the match between a real face and an imaginary face.

It is a further objective of the present invention to provide a method and system that uses real-time measurements of cerebral blood flow velocity in major arteries of the brain for example middle cerebral arteries to measure the response to a composite illustration of a face.

It is a further objective of the present invention to provide a method and system that uses real-time measurements of cerebral blood flow velocity in major arteries of the brain for example middle cerebral arteries to measure the response to a composite illustration of a face as matched to a target imaginary face.

It is a further objective of the present invention to provide a method and system that uses real-time measurements of cerebral blood flow velocity in major arteries of the brain for example middle cerebral arteries to measure the response to an affective expression of a face.

It is a further objective of the present invention to provide a method and system that uses real-time measurements of cerebral blood flow velocity in major arteries of the brain for example middle cerebral arteries to measure the response of enhancement of a face using hairstyle, color of clothing, and skin tone.

It is a further objective of the present invention to provide a method and system that uses real-time measurements of cerebral blood flow velocity in major arteries of the brain for example middle cerebral arteries to measure the response of a makeup face as matched to a target face.

It is a further objective of the present invention to provide a method and system that uses real-time measurements of cerebral blood flow velocity in major arteries of the brain for example middle cerebral arteries to measure the response to a composite illustration of a face as matched to a target face.

It is a feature of the present invention to provide a method and system that uses real-time measurement of a cerebral blood flow velocity in major arteries of the brain for example middle cerebral arteries to measure the response to a face for example of a potential model as matched to a target face for example a very successful model.

It is a further feature of the present invention to provide a method and system that uses real-time measurement of a cerebral blood flow velocity in major arteries of the brain for example middle cerebral arteries to measure the response of facial features desired by a person wishing to undergo plastic surgery for example an actress to matched the sex appeal of a target face for example the face of a very successful actress.

It is a further feature of the present invention to provide a method and system for measuring face working memory in crime scene witness or in a patient with brain lesion.

It is a further objective of the present invention to provide a method and system that uses real-time measurements of cerebral blood flow velocity in major arteries of the brain for example middle cerebral arteries to measure object recognition.

It is a further objective of the present invention to provide a method and system that uses real-time measurements of cerebral blood flow velocity in major arteries of the brain for example middle cerebral arteries to measure the response to an imaginary object.

It is a further objective of the present invention to provide a method and system that uses real-time measurements of cerebral blood flow velocity in major cerebral arteries of the brain for example the middle cerebral arteries to determine the match between a real object and the imaginary object seen by the witness of a crime scene.

It is a further objective of the present invention to provide a method and system that uses real-time measurements of cerebral blood flow velocity in major arteries of the brain for example middle cerebral arteries to measure the response to a composite illustration of an object.

It is a further objective of the present invention to provide a method and system that uses real-time measurements of cerebral blood flow velocity in major arteries of the brain for example middle cerebral arteries to measure the response to a composite illustration of an object as matched to a target imaginary object.

It is a further objective of the present invention to provide a method and system that uses real-time measurements of cerebral blood flow velocity in major arteries of the brain for example middle cerebral arteries to measure the response to an object for example a new product and matched to the response evoked by a very successful product.

It is a feature of the present invention to provide a method and system that uses real-time measurements of cerebral blood flow velocity in major arteries of the brain for example middle cerebral arteries to measure the response of enhancement of an object such as a new brand of car using color, size and form of the object and matching it to the response evoked by a target object for example a successful brand of car.

It is a further feature of the present invention to provide a method and system for measuring object working memory in crime scene witness or in a patient with brain lesion.

These and other objects of the invention may become more apparent to those skilled in the art upon reviewing the description of the invention as set forth hereinafter, in view of its drawings

DETAILED DESCRIPTION OF THE INVENTION

Figure 1:
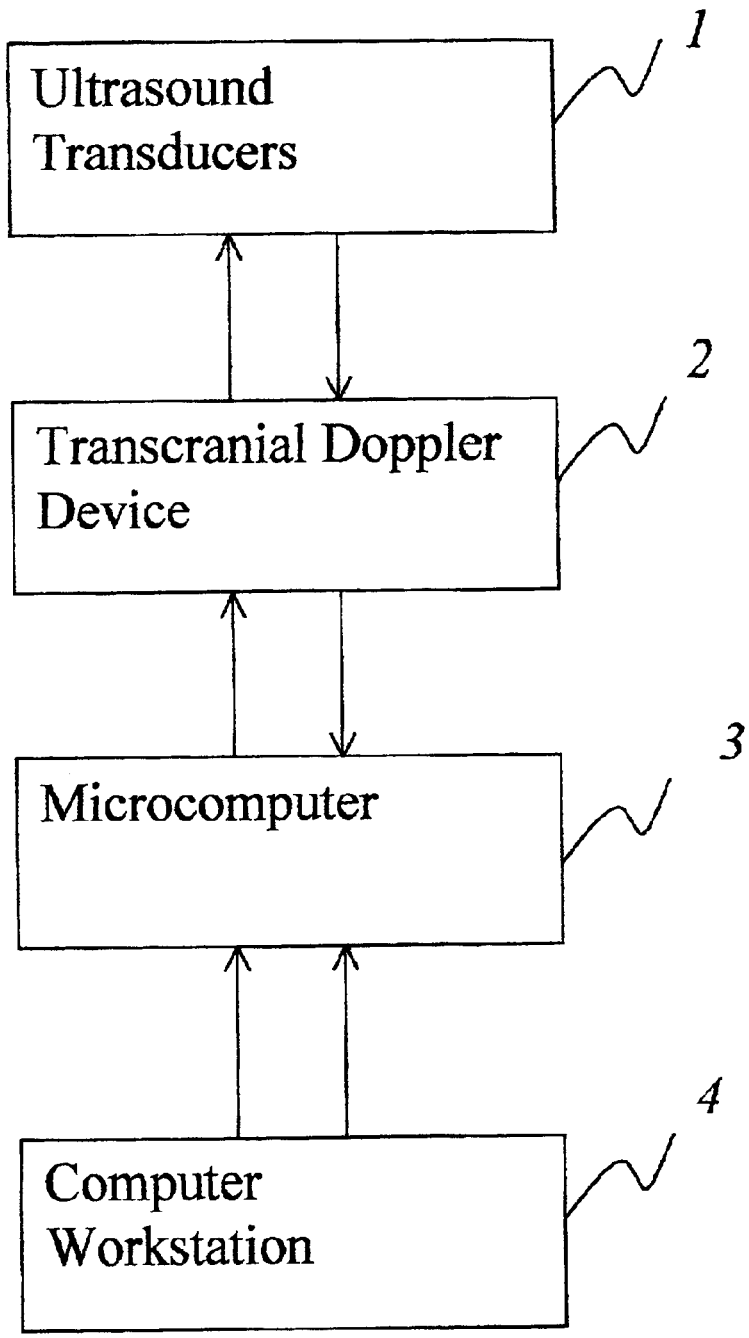
FIG. 1 is a block diagram schematically representing the present invention.

The block diagram of the present invention is illustrated in FIG. 1. As shown therein, a head set with ultrasound transducers 1, is placed on a human subject who wears the head set with two transcranial Doppler probes attached and focused on the cerebral arteries for example the middle arteries (MCAs) from both sides of the head on the temporal bones above the zygomatic arch. The sample volumes of the pulsed Doppler could be placed at a depth of 50 mm from the surface of the probe on both sides. The probes are covered with ultrasonic gel to enhance tissue coupling. The headset steers the probe by manual or automated insonation of the cerebral vessels and is controlled by a microcomputer 3 connected with the transcranial Doppler instrument (TCD) 2. The TCD instrument 2 with bilateral probes is a miniaturized version operatively controlled by a microcomputer 3 and could be from a company called DWL Slipplingen, Germany) by way of example. The microcomputer 3 communicates with the main computer workstation 4 for example the Federal Bureau of Investigation (FBI) crime database, to retrieve information on faces of criminals in the database or to another remote computer with capability for image processing.

Figure 2:
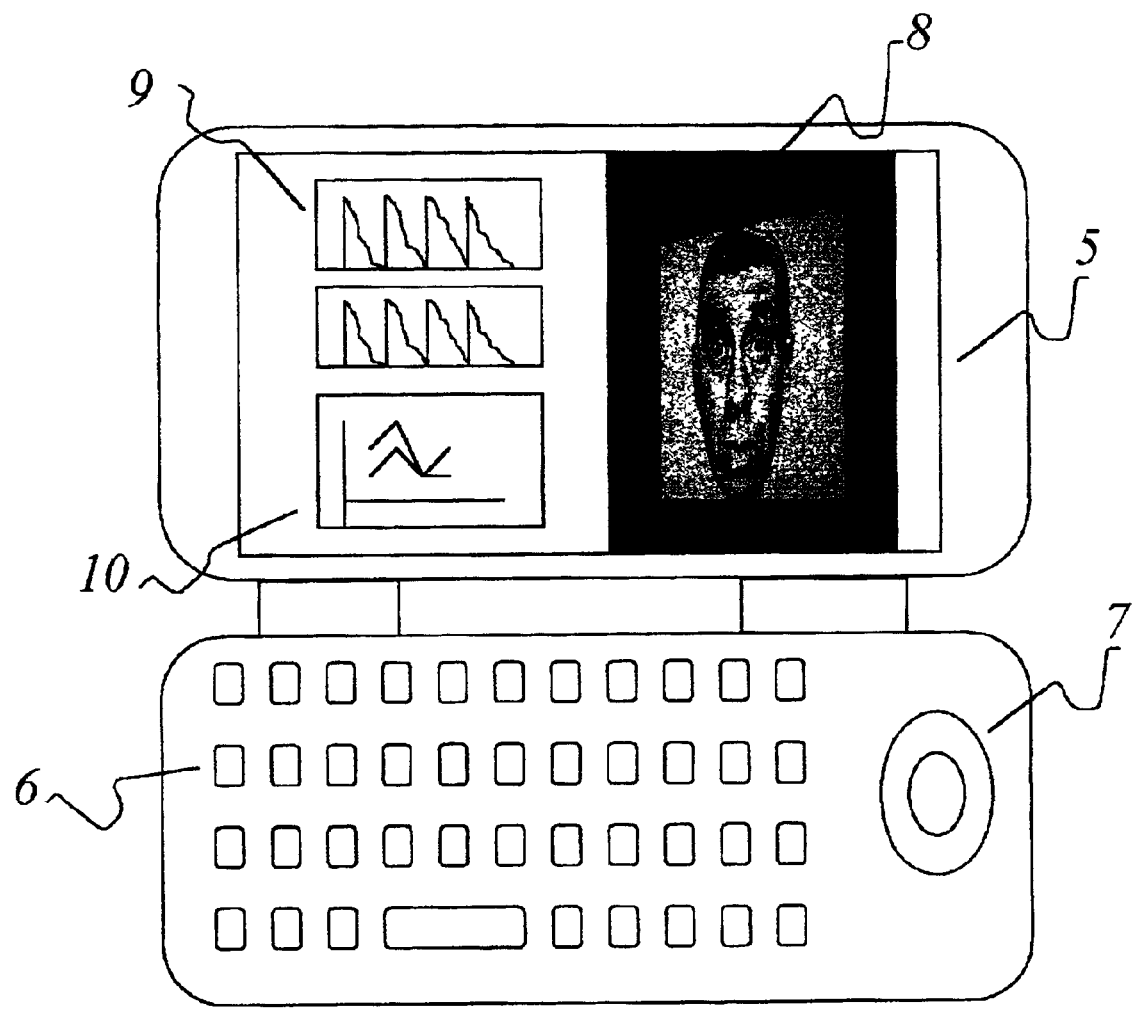
FIG. 2 is a schematic representation of one possible embodiment of the present invention.

As shown in FIG. 2, the TCD instrument has the normal features of a computer with a monitor display 5, a keyboard 6, and a loudspeaker 7 to produce audible Doppler signals. The computer monitor displays the images such as a face 8 and Doppler flow velocity profiles 9 from the left and right middle cerebral arteries by way of example. The trend velocities and calculated laterality index are displayed below 10 with the choice to select specific time segments for further analyses.

Figure 3:
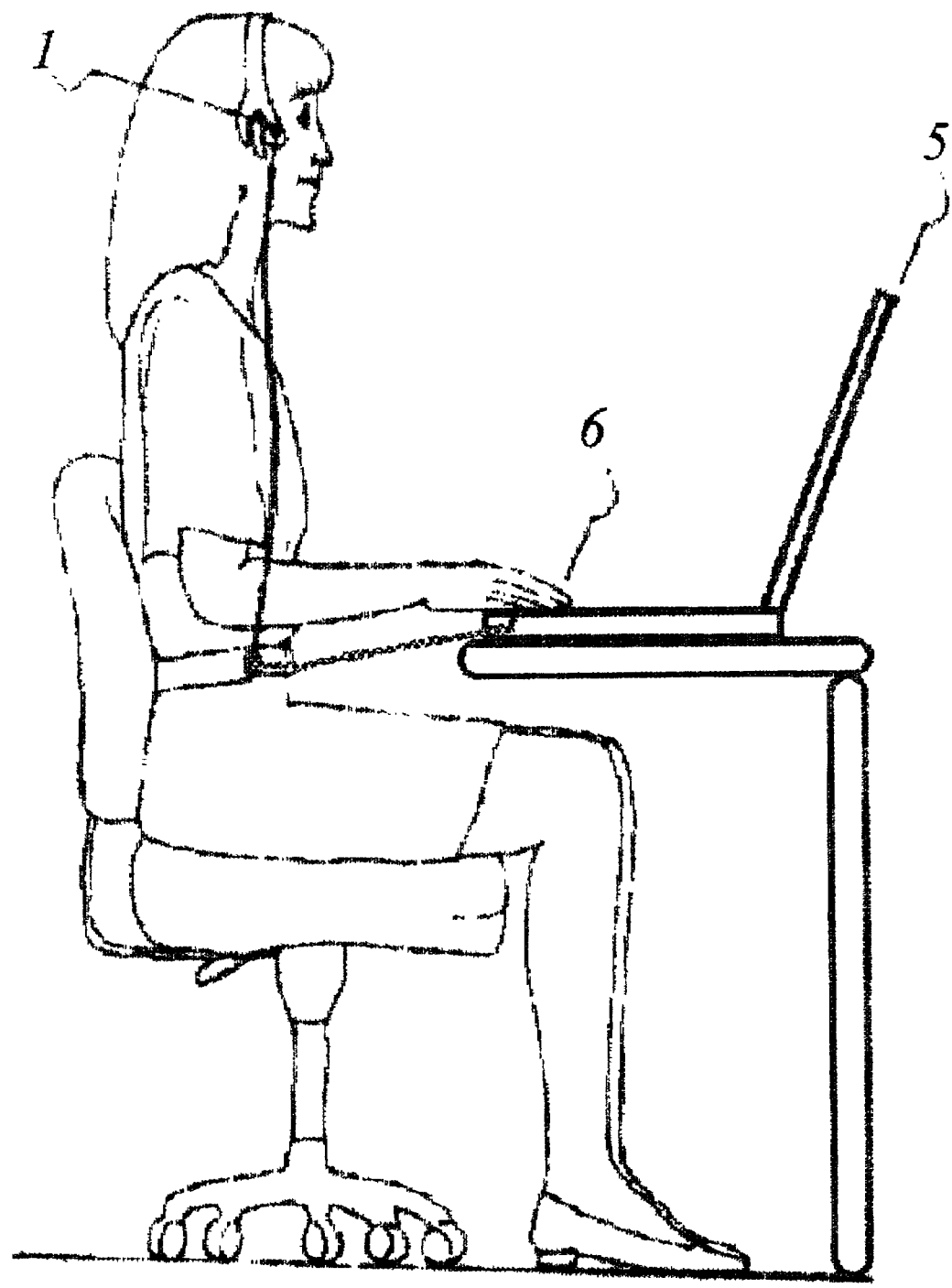
FIG. 3 shows the interface of the invention with a subject.

FIG. 3 shows the interface of the invention with a subject. The headset is placed on the head with ultrasound transducers 1 held in place in the left and right arms of the headset and placed on the left temporal and right temporal bones of the head. The transducer cable is attached to the TCD instrument. While the device is in use the subject could make inputs into the computer keyboard 6 for example scroll through a given image or provide a non-verbal response by tapping a key on the keyboard 6 as he/she watches the monitor 5.

Figure 4:
FIG. 4 shows images that could be presented to the subject on the computer monitor.

FIG. 4 shows the images that could be presented to the subject. An object 11 could be presented as well as faces. Face reconstruction could begin with a sketchy outline of the face 12 and then a face with a quarter of the features presented in the appropriate manner 13 and then half of the features could be presented 14 and so on until a threshold is reached that will enable recognition of the target neutral face 15. The response to varying expressions of the neutral face 15 such as sad face 16 or happy face 17 could facilitate obtaining a much closer match to the cerebral blood flow velocity response pattern of the imaginary face held in memory.

Figure 5:
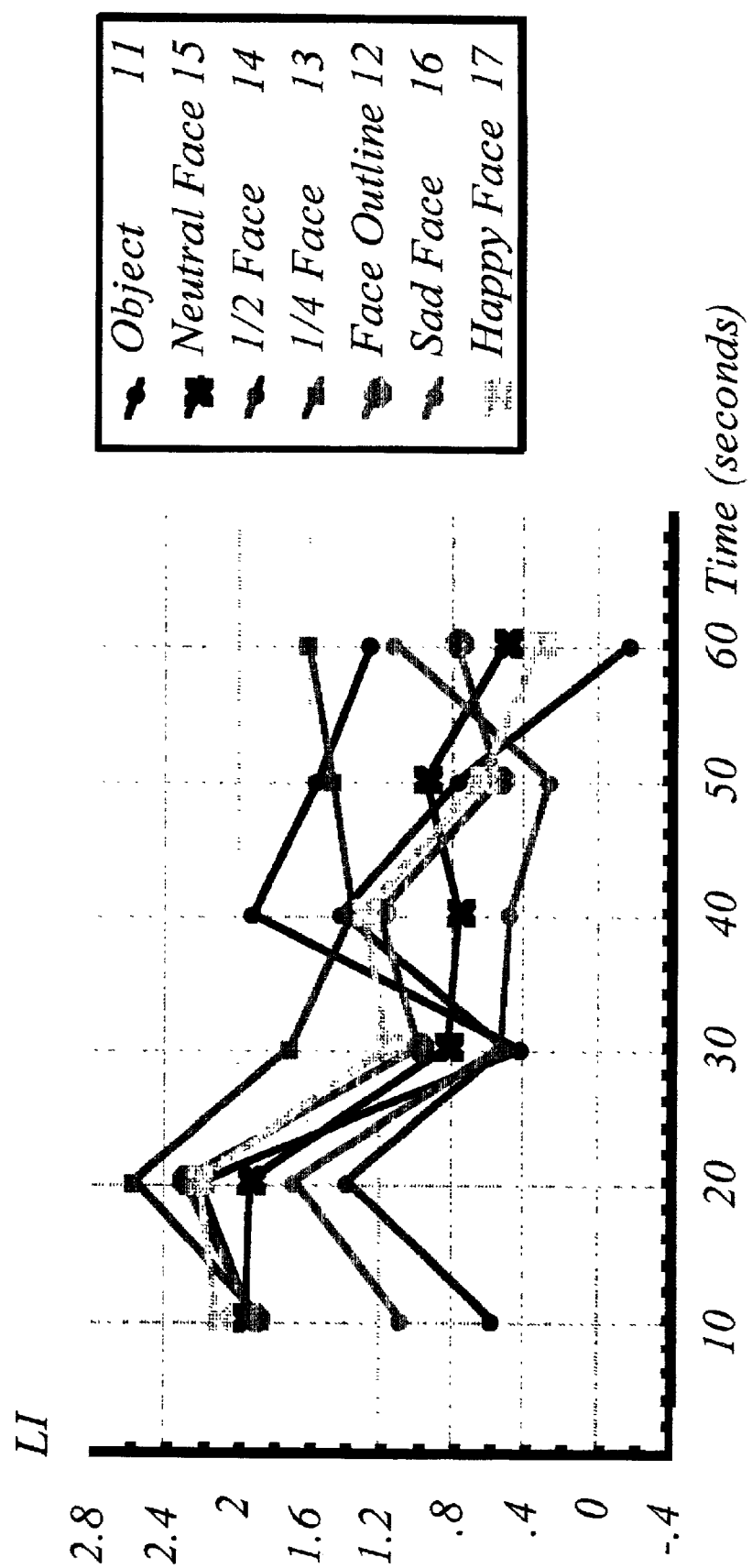
FIG. 5 shows the plot of mean laterality index (LI) changes in males during the presentation of several images.

FIG. 5 shows the plot of mean laterality index (LI) changes in males during the presentation of several images. A detailed description of an experiment to determine the LI during object and face perception tasks illustrated in FIG. 4 is set forth below.

Materials and Methods

Simultaneous bilateral TCD ultrasound was used to measure mean blood flow velocities (MBFV) in the right and left middle cerebral arteries (MCA) in right-handed normal subjects. The preferred hand was determined using the Edinburgh handedness inventory. The population consisted of 24 subjects (mean±SD age=25.12±3.21 years) of which 15 were females (mean±SD age=25.53±3.58 years) and 9 were males (mean±SD age=24.44±2.61 years). There was no history of neurologic or cardiovascular or respiratory diseases in the study cohort. No subject had any history of long use of any medication. None ingested caffeine at least 24 hours prior to the study. All were non-smokers and had no history of alcohol abuse. All have had 16 18 years of schooling. Informed and signed consent was provided to all subjects according to the Declaration of Helsinki, and the Institutional Ethical Committee guidelines.

Scanning Procedure. All TCD procedures were performed using examination techniques described for cognitive studies. The transcranial Doppler scanning was performed using a new bilateral simultaneous TCD instrument (Multi-Dop T, DWL, Sipplingen, Germany). All subjects were briefed on the protocol for the entire experiment and all questions and practice sessions on what was required for the facial paradigm were explained prior to start of the experimental data acquisition. All TCD studies were performed as follows: first, the subject was placed in supine posture with head up at 30 degrees. The probe holder headgear -LAM Rack was used with base support on two earplugs and on the nasal ridge. Two 2 MHz probes were affixed in the probe holder and insonation performed to determine the optimal position for continuous insonation of both MCA main stems at 50 mm depth from the surface of the probe. All gain and power settings were kept constant for both MCAs in all subjects. The probes were placed firmly on the subjects head and were locked in position after adjusting the lever and tightening the knurled screw from both sides. Comfort of the subject within the headgear was assured prior to start of recording. Subjects were instructed to remain mute and not to move throughout the data acquisition time duration. All environmental noise including sound from the TCD instrument was excluded, and environmental luminance was kept constant for all participants. Electrocardiographic monitoring of pulse and respiratory rate along with self-perceived anxiety levels were recorded during the study to control for effects on results.

Baseline study. The baseline condition was dark. This was achieved by having the subject view through a 3-D View Master, International group Inc. Portland, Oreg. with all its inside walls colored with black paint, and the back view covered with a dark slide. As a result the subject had full binocular view of a dark background while holding the view master in place with both hands, and avoiding interference with the probe holder at the nasal ridge. A continuous train of velocity waveform envelopes was recorded at resting baseline with the subject mute, still and attention focused within a dark visual field projected in a 3-D View-Master with no mental or manual tasks to perform. These baseline recordings were obtained prior to stimuli administration. TCD baseline measurements were made for 60 seconds.

Black and white checkered Square Paradigm. The black and white checkered square paradigm 11 (see FIG. 4) comprised a square of alternating black and white square dots. This was a nonverbal passive viewing task of a foveally presented square from a slide projector onto a screen placed in front of the subject inclined at 30 degrees from the horizontal plane at a distance of 80 cm from the nasal ridge. A continuous train of velocity waveform envelopes was recorded with the subject mute, still and attention focused on the square with no mental or manual tasks to perform. TCD baseline measurements were made for 60 seconds.

Facial Paradigm

The black and white facial paradigms 12–17 are shown and described in FIG. 4. In addition inverted variations of faces 12–14 were presented to examine inversion effects. Each subject was instructed to study the novel neutral face 15 presented in upright view and remember the facial features for comparison with subsequent tasks. Subjects were given instructions to mentally reconstruct the degraded faces using the original sample neutral face as target match. For tasks 16 and 17, subjects were asked to judge affect of the presented faces considering that the sample face stimulus 12 is neutral. A brief training session was provided before the actual experimental runs by way of example. All tasks were performed with fixed eye gaze. The subjects were not instructed to use any specific strategy to rearrange the faces or fill-in missing parts of the deleted faces however; they were warned to refrain from verbalization both audibly or internally. Environmental noise was excluded and lighting keep at a constant during the facial paradigm.

Calculations. Cerebral lateralization was assessed by side-to-side differences in mean flow velocity given as laterality index (LI') by way of example and expressed as:

$$LI'=(\text{Right } MBFV_{10sec}-\text{Left } MBFV_{10sec}/(\text{Right } MBFV_{10sec}+\text{Left } MBFV_{10sec}))*100.$$

The actual magnitude of lateralization (LI) for each 10 seconds segment for each task was calculated as the difference between LI values measured during the 10 seconds segment of the task and the corresponding 10 seconds segment of rest (onset of resting baseline corresponds with onset of visual task within the 60 seconds):

$$LI=LI'\text{task}_{10sec}-LI'\text{rest}_{10sec}.$$

In general, positive LI values suggest right lateralization, while negative LI values suggest left lateralization. Zero LI values showed no lateralization from the resting condition or possible bilateral response. The calculated LI were designated as $LI_{0-10sec}$, $LI_{11-20}\text{sec}$, $LI_{12-30sec}$, $LI_{41-50sec}$, $LI_{41-60sec}$, $LI_{51-60sec}$, for values measured for the time segment 0–10 seconds, 11–20 seconds, 21–30 seconds, 31–40 seconds, 41–50 seconds, 51–60 seconds respectively.

Statistics. Results were given as mean±SD where applicable. To examine the effect of Time variable, the LI scores were analyzed by a 2-way analysis of variance (ANOVA) for repeated measures. The resulting design was a 2 (Gender: Female, Male) by 6 (Time periods of 10 seconds each: 0–10s, 11–20s, 21–30s, 31–40s, 41–50s, 51–60s intervals), the latter factor was a within-subject or repeated measures factor because it represents repeated measures at different time intervals in the same subject. To examine the effect of Task variable, the LI values were further analyzed in a separate 3-way ANOVA for repeated measures. The resulting design was a 2 (Gender: Female, Male) by 6 (Time periods of 10 seconds each) by 10 (Tasks 1–10) ANOVA. The last two factors are within-subject or repeated measures factors because they represent repeated measurements of the effects of different tasks at different time intervals on the same subject. The first factor is a between-group factor because subjects were either female or male subjects. All statistical calculations were performed using a statistical software package (Statistica, StatSoft, OK, USA).

Results

The results were analyzed for all 10 facial tasks (including 3 for inversion effects), however, the response in the seven basic tasks including object and face paradigms were plotted on FIG. 5. The initial two-way ANOVA with repeated measures with design of 2 (Gender) by 6 (Time) revealed a significant main effect of Gender $F(1,238)=27.7$, $p<0.0000003$, MSe=477.6. There was a significant main effect of Time $F(5,1190)=15.98$, $p<0.00000001$, MSe=40.8. There was a Gender×Time interaction $F(5,1190)=2.68$, $p<0.02$. The second three-way ANOVA with repeated measures with design of 2 (Gende6 by 6 (Time) by 10 (Tasks). When all 10 Tasks and 6 Time factors were combined in the design the Gender factor was not significant $p>0.05$. All 10 Task factors when used in the design did not show a significant ($p>0.05$) difference. Therefore, a planned contrast was then performed to examine if changes at a given Time segment varied across the Tasks in males and females. Further analysis of laterality index variations examined the latency (time of occurrence of a peak) and peak value of right and left lateralization during a given task. Selection of peak right lateralization at 20 seconds from the onset of the task (P20) and peak left lateralization at 40 seconds from onset of the task (P40), showed a significant Gender related difference in a separate planned contrast, F(1,22)=4.7; MSe=2–75; p<0.04. Using P20 and P40 peaks in further planned contrasts did not reveal any significant difference related to Tasks among Female subjects p>0.05. On the other hand there was a significant effect among male subjects F(1,22)=8.3; MSe=485; p=0.008. Further analyses using P20 and P40 was undertaken for the different Tasks among male subjects. The results of the planned contrasts between each pair of Tasks were statistically significant (p<0.05) except for the comparison between neutral face 15 and half face 14 (p>0.05). This may suggest that as the composite face recreates half the facial features the subjects cerebral blood flow velocity response became similar to that evoked by neutral face 15. The happy and sad faces differed significantly (p<0.05). One possible application of this distinction is that by varying affect, the significant distinction evoked by unpleasant or pleasant facial expression could be related to the facial expression associated with a particular crime scene by way of example. In this study (FIG. 5) sad face 16 was associated with a relative left shift in cerebral lateralization as compared to neutral face 15 and happy face 17. The recruitment of additional emotionally related centers in the left hemisphere could have accounted for the differences in the responses to sad and happy faces. There was a significant effect (p<0.05) due to inversion of the faces.

Figure 6:
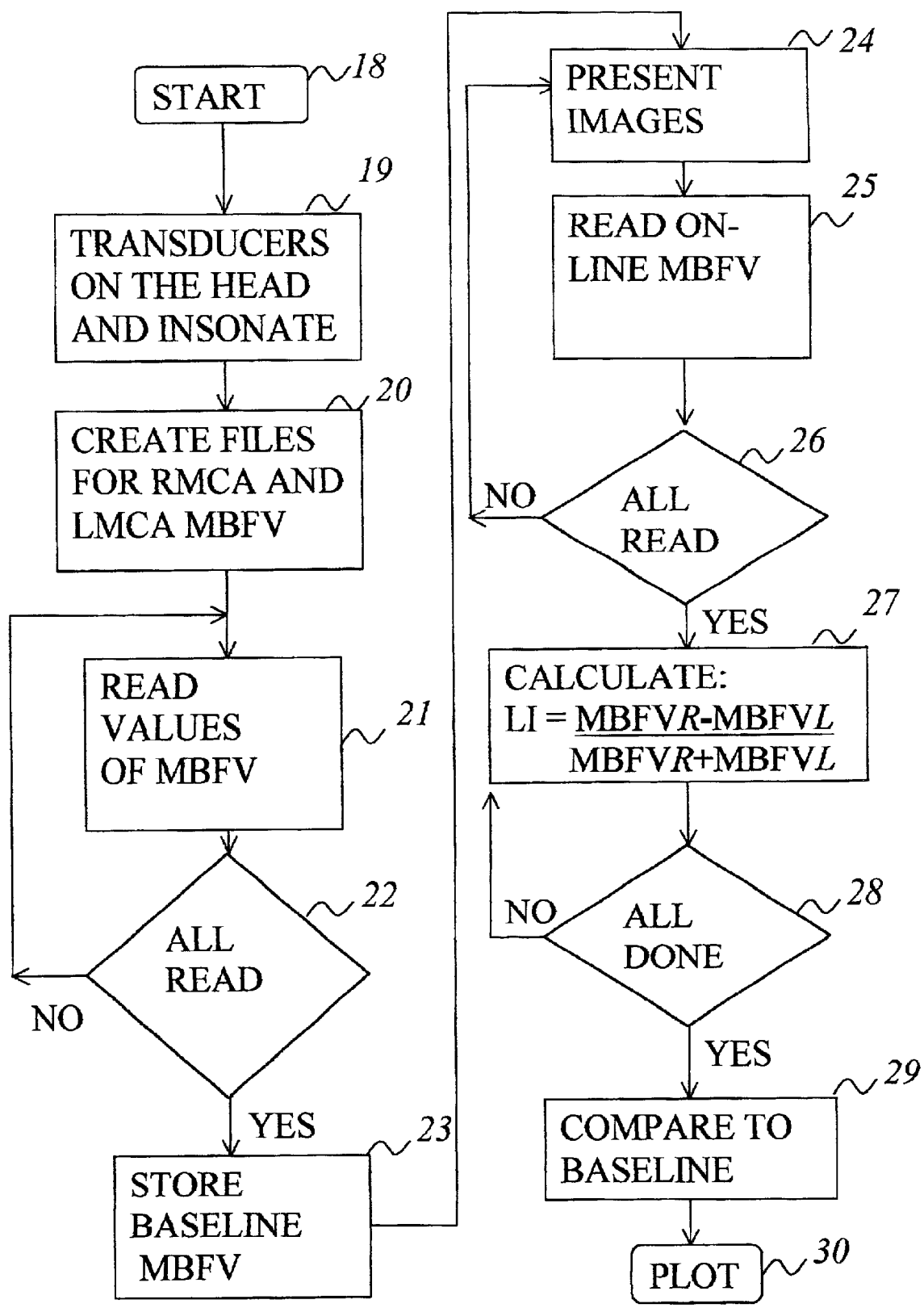
FIG. 6 is an example of a functional flow chart of the present invention.

The functional flow chart of the present invention by way of example is seen in FIG. 6. After the setup 18 of the headset and the device of the present invention as shown in FIG. 3 both MCAs are monitored using the ultrasound transducers 19 and the MBFV determined at a depth of 50 mm and files created for the specific recording 20. The values of MBFV determined from flow velocity waveforms of good Doppler signal quality are read 21. If all are read 22 the system proceeds to store these values as baseline 23 depending on what condition the investigators chooses for example, simple eye closure could be used as baseline. The images are then presented sequentially to the subject on the computer monitor 24 and the MBFV measured during perception of the image(s). All images and the corresponding MBFVs are read 25. If not, the image presentation sequence is completed and the corresponding blood flow velocities recorded 26, and the system proceeds to calculate the LI for baseline and online measured MBFV in the right (MBFVR) and left (MBFVL) middles cerebral arteries 271 given by the formula (see also below):

$$LI' = (MBFVR_{10sec} - MBFVL_{10sec}/(MBFVR_{10sec} + MBFVL_{10sec}))*100.$$

An LI value is derived for each image presented sequentially. If not 28 all have been determined then the system continues with the calculation for each image 27. If all have been calculated then the system proceeds to determine the LI for baseline and compares it with the online (task-related) LI values. The calculation of the relative change in LI 29 is given by:

$$LI'LI'task_{10sec} - LI'baseline_{10sec}.$$

The derived values are then plotted 30 on the computer monitor for further analysis similar to that on FIG. 5.

While a preferred embodiment of the present invention is described above, it is contemplated that numerous modifications may be made thereto for particular applications without departing from the spirit and scope of the present invention. Accordingly, it is intended that the embodiment described be considered only as illustrative of the present invention and that the scope thereof should not be limited thereto but be determined by reference to the claims hereinafter provided.

I claim:

1. A noninvasive method to determine the cerebral blood flow velocity response to face recognition tasks of a human subject, including steps of:
    (a) obtaining a subjects baseline cerebral blood flow velocity in cerebral arteries on both sides of the brain using a transcranial Doppler ultrasound instrument with two probes placed on the temples and sample volumes focused on cerebral vessels on both sides;
    (b) simultaneously with (a) obtaining the mean blood flow velocity in both pairs of cerebral arteries at baseline;
    (c) testing the subject with face recognition tasks on the screen of a digital computer and using a computer input peripheral device while simultaneously monitoring the mean blood flow velocity during each stage of the task in real-time;
    (d) determining the response of the brain using mean cerebral blood flow velocity to a particular imaginary or real face;
    (e) determining the response of the brain using side-to-side differences in mean cerebral blood flow velocity to a given target face;
    (f) determining the response of the brain using side-to-side differences in mean cerebral blood flow velocity to a given composite face;
    (g) determining the response of the brain using side-to-side differences in mean cerebral blood flow velocity to a given facial expression;
    (h) simultaneously with (g) determining if there is a match of the response of the brain using side-to-side differences in mean cerebral blood flow velocity to a given face compared to the response evoked by target face; and
    (i) simultaneously with (h) assessing if by varying the emotional expression of the given face the match in response to target face could be enhanced.

2. The invention of claim 1 wherein the said device is operatively connected to a microcomputer that processes and displays the cerebral blood flow velocity signals, latorality indices and faces.

3. The invention of claim 2 wherein the cerebral blood flow velocity is used to determine all three phases of facial processing including the initial formation of a percept originating from the given face matching the percept to preexisting stored information and a contextual nonverbal and/or verbal evocation.

4. The invention of claim 3 wherein the cerebral blood flow velocity is used to determine if a given alteration on a face evokes a brain response that matches a particular target face or not.

5. The invention of claim 4 wherein the subject is processing a facial task displayed on a screen of a digital computer retrieved from a computer workstation.

6. The invention of claim 5 and further including a computer workstation means for retrieving the faces from a forensic database.

7. The invention of claim 5 and further including a computer workstation means for retrieving faces from an advertising database.

8. The invention of claim 5 further including a computer workstation means for facial reconstruction for purposes of performing plastic surgery.

9. A noninvasive method to determine the cerebral blood flow velocity response to object recognition tasks of a human subject, including steps of:

(a) obtaining a subjects baseline cerebral blood flow velocity in cerebral arteries on both sides of the brain using a transcranial Doppler ultrasound instrument with two probes placed on the temples and sample volumes focused on cerebral vessels on both sides;

(b) simultaneously with (a) obtaining the mean blood flow velocity and laterality index at baseline;

(c) testing the subject with object recognition tasks on the screen of a digital computer and using a computer input peripheral device while simultaneously monitoring the mean blood flow velocity during each stage of the object task in real-time;

(d) determining the response of the brain using the laterality index calculated from mean cerebral blood flow velocity to a particular imaginary object;

(e) simultaneously with (d) determining the latency and peak variations of laterality index during each task;

(f) determining the response of the brain using the latency and peak variations of laterality index calculated from mean cerebral blood flow velocity to a given target object;

(g) determining the response of the brain using the latency and peak variations of laterality index calculated from mean cerebral blood flow velocity to a given composite object;

(h) determining the response of the brain using the laterality index calculated from mean cerebral blood flow velocity to a given color of the object;

(i) simultaneously with (h) determining if there is a match of the response of the brain using the latency and peak variations of laterality index calculated from mean cerebral blood flow velocity to a given object to the response evoked by target object; and (j) simultaneously with (i) assessing if by varying the form and size of the given object the match in response to target object is enhanced.

10. The invention of claim 9 wherein the said device is operatively connected to a microcomputer that processes and displays the cerebral blood flow velocity signals, laterality indices and objects.

11. The invention of claim 10 and further including using the responses of cerebral blood flow velocity to determine the effects of change in object size, form or color compared to a target object.

12. The invention of claim 10 and further including using the responses of cerebral blood flow velocity to determine the effect of change in features of a particular product compared to a target product.

13. The invention of claim 10 and further including means for measuring object working memory in a subject or patient with brain lesion.

14. A noninvasive method to determine the cerebral blood flow velocity response to face recognition tasks of a human subject, including steps of:

(a) obtaining a subjects baseline cerebral blood flow velocity in cerebral arteries on both sides of the brain using a transcranial Doppler ultrasound instrument with two probes placed on the temples and sample volumes focused on cerebral vessels an both sides;

(b) simultaneously with (a) obtaining the mean blood flow velocity and laterality index at baseline;

(c) testing the subject with face recognition tasks on the screen of a digital computer and using a computer input peripheral device while simultaneously monitoring the mean blood flow velocity during each stage of the facial task in real-time;

(d) determining the response of the brain using the laterality index calculated from mean cerebral blood flow velocity to a particular imaginary or real face;

(e) simultaneously with (d) determining the latency and peak variations of laterality index for each task;

(f) determining the response of the brain using the latency and peak variations of laterality index calculated from mean cerebral blood flow velocity to a given target face;

(g) determining the response of the brain using the latency and peak variations of laterality index calculated from mean cerebral blood flow velocity to a given composition face;

(h) determining the response of the brain using the latency and peak variations of laterality index calculated from mean cerebral blood flow velocity to a given facial expression;

(i) simultaneously with (h) determining if there is a match of the response of the brain using the latency and peak variations of laterality index calculated from mean cerebral blood flow velocity to a given face compared to the response evoked by target face;

(j) simultaneously with (i) assessing if by varying the emotional expression of the given face the match in response to target face could be enhanced; and (k) simultaneously with (j) assessing faces retrieved from a computer workstation operatively connected to a microcomputer.

15. The invention of claim 14 wherein the brain responses to facial makeup are used to optimize the look of a given face in comparison to a target face.

16. The invention of claim 14 wherein the brain responses to addition or removal of a facial feature are used to optimize the look of a given face in comparison to a target face.

17. The invention of claim 14 wherein the brain responses to posture of a given face are used to optimize the look of a given face in comparison to a target face.

18. The invention of claim 14 wherein the brain responses to a particular facial expression are used to optimize the look of a given face in comparison to a target face.

19. The invention of claim 14 wherein the brain responses to hairstyle accompanying a given face are used to optimize the look of a given face in comparison to a target face.

20. The invention of claim 14 and further including means for measuring face recognition working memory in a subject or patient with brain lesion.

* * * * *